(12) United States Patent
Erdogan et al.

(10) Patent No.: US 6,211,957 B1
(45) Date of Patent: Apr. 3, 2001

(54) IN-LINE ALL-FIBER POLARIMETER

(75) Inventors: Turan Erdogan, Spencerport, NY (US); Thomas Andrew Strasser, Warren; Paul Stephen Westbrook, Chatham, both of NJ (US)

(73) Assignee: Lucent Technologies, Inc., Murray Hill, NJ (US)

( * ) Notice: Subject to any disclaimer, the term of this patent is extended or adjusted under 35 U.S.C. 154(b) by 0 days.

(21) Appl. No.: 09/517,865

(22) Filed: Mar. 3, 2000

(51) Int. Cl.⁷ .................................................. G01J 4/00
(52) U.S. Cl. .................... 356/364; 356/367; 356/366; 385/11
(58) Field of Search .................... 356/364, 366, 356/367; 385/11, 115

(56) References Cited

U.S. PATENT DOCUMENTS 5,440,390   8/1995   Tirri .
5,815,270 * 9/1998   Lee ..................................... 356/367

OTHER PUBLICATIONS

Ahmed Bouzid, Mustafa A.G. Abushagur, A&D El–Sabae, R.M.A. Azzam "Fiber Optic Four–Detector Polarimeter" Optics Comm. Jul. 15, 1995.

* cited by examiner

Primary Examiner—Frank G. Font
Assistant Examiner—Roy M Punnoose

(57) ABSTRACT

An in-line optical fiber polarimeter comprises a plurality of fiber gratings and a single wave plate, disposed sequentially along a length of optical fiber. The fiber gratings are precisely oriented and have a predetermined grating period such that each grating functions to out-couple a predetermined portion of the optical signal passing through the polarimeter. A separate detector is associated with each grating to measure the out-coupled signal. The four Stokes parameters can be determined from the set of measurements and then used to determine to state of polarization of an optical signal passing through the polarimeter.

24 Claims, 3 Drawing Sheets

IN-LINE ALL-FIBER POLARIMETER

TECHNICAL FIELD

The present invention relates to a polarimeter and, more particularly, to an in-line., all-fiber polarimeter for measuring the state of polarization (SOP) of a propagating lightwave signal.

BACKGROUND OF THE INVENTION

As a result of the inherent degeneracy associated with the polarization of light traveling in an optical fiber, it is often important to be able to measure the state of polarization (SOP) of an optical signal at a given point in time and space. Polarization measurement is important, for example, in accurately orienting polarization maintaining fiber during a splicing operation, in measuring the polarization dependent loss (PDL) of components or systems, as well as in determining the polarization-mode dispersion (PMD) in optical transmission systems. Polarization mode dispersion is an increasingly critical phenomenon that will need to be controlled with high precision in the emerging high-speed (multi-Gbps), long-haul systems.

Most prior art arrangements for measuring polarization mode dispersion rely on a statistical sampling of polarization states. See, for example, U.S. Pat. No. 5,440,390 issued to Tirri et al. on Aug. 8, 1995. As networks grow increasingly complex, especially with the advent of local access, optical signal monitoring will become more important to ensure reliable operation. Real-time measurement of polarization mode dispersion and correlation of this data with bit-error rate (BER) or system quality would be a useful tool in measuring the optical system performance. Moreover, some processes could be improved, or at least made more deterministic, if a simple in-line technique were available for providing knowledge of the exact state of polarization within the transmission fiber.

An exemplary prior art "in-line" fiber optic polarimeter is described in an article entitled "Fiber-optic four-detector polarimeter" by A. Bouzid et al. appearing in *Optics Communications*, Vol. 18, 1995, at pp. 329–324. In the Bouzid et al. arrangement a set of four externally-induced, in-core fiber gratings are used in association with four photodetectors to perform the polarization measurements. The article purports to provide for the measurement of all four Stokes parameters simultaneously by measuring the intensity of light absorbed (or reflected or transmitted) by four photodetectors at four different planes of incidence. However, the arrangement lacks any phase retardation element, which is necessary in order to accurately define the required Stokes parameters. Additionally, this polarimeter lacks sufficient bandwidth to be useful in telecommunications applications.

Thus, a need remains in the art for an in-line polarization measurement device that is readily available for use in systems, particularly where it could be combined with a polarization controller to enable polarization-sensitive devices or functions to be utilized.

SUMMARY OF THE INVENTION

The need remaining in the prior art is addressed by the present invention, which relates to a polarimeter and, more particularly, to an in-line, all-fiber polarimeter for measuring the state of polarization (SOP) of a propagating lightwave signal.

In accordance with the present invention, an in-line, all-fiber polarimeter comprises a plurality of gratings formed in the fiber itself which, when coupled with fiber birefringence (phase retardation), is capable of coupling light out of the fiber in a highly polarization-selective fashion. A plurality of detectors are disposed near (or on) the outside of the fiber and are used to receive the outcoupled radiation. The polarization state of the fiber can then be ascertained, in real time, by reviewing the readings on the plurality of detectors. In general, a set of four gratings, in combination with a single elliptical retardation element, can be used to precisely define the polarization state of the optical signal.

In one embodiment of the present invention, a first blazed grating formed within the fiber is used to out-couple a first, predetermined polarization. Disposed beyond the first grating is a second blazed grating oriented to out-couple a second, orthogonal polarization. A third blazed grating is linearly polarized and disposed to out-couple light at an angle of 45° with respect to the first two output beams, thus measuring both polarization components. The remaining optical signal then passes through a birefringent section of fiber whose principle axis is at 0°, after which another measurement of linear polarization at 135° is made. The set of four measurements can be used to calculate the set of well-known Stokes parameters $S_1$–$S_4$ and thus determine the state of polarization (SOP) of the transmission fiber.

In a preferred embodiment of the present invention, the gratings are disposed at a blaze angle of 45° to optimize the out-coupled signal at the polarization sensitive angle of 90°.

Preferably, the blazed gratings of the in-line all-fiber polarimeter of the present invention are formed using an interferometric technique with an excimer-pumped, frequency-doubled, pulsed dye laser. Other alternatives are possible.

Various other aspects of the present invention will become apparent during the course of the following discussion and by reference to the accompanying drawings.

BRIEF DESCRIPTION OF THE DRAWINGS

Referring now to the drawings.

DETAILED DESCRIPTION

Figure 1:
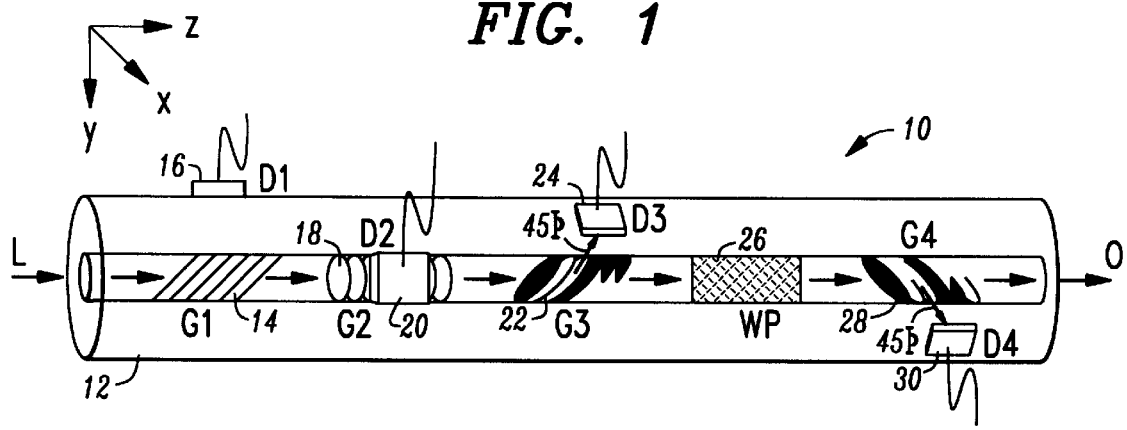
FIG. 1 illustrates an exemplary in-line, all-fiber polarimeter formed in accordance with the present invention.

Prior to describing the specific in-line all-fiber polarimeter of the present invention, it is useful to provide a clear definition of "state of polarization" (or SOP), with respect to an optical signal propagating through a fiber. In general, if the core-cladding index difference in a given optical fiber is sufficiently small, then the electric field associated with a particular mode in the fiber may be written as:

$$E(z,t) = \hat{x} A_x \exp(i\phi_x) + \hat{y} A_y \exp(i\phi_y)$$

where $A_x$ and $A_y$ define the relative magnitude of each vector component and the phases are defined as follows:

$$\phi_x = \beta z - \omega t + \phi_0, \text{ and}$$

$$\phi_y = \beta z - \omega t + \phi_0 - \delta,$$

where $\beta$ defines the propagation constant, $\omega$ defines the angular frequency, $\phi_0$ defines an arbitrary phase value, and $\delta$ is the relative phase difference between the two orthogonal components of the electric field.

In accordance with the teachings of the present invention, the state of polarization (SOP) of an optical fiber will be described using the Jones calculus and the Stokes parameters, since these are both complete and commonly used. In terms of equation (1), the Jones vector J that describes the field at any location z or point in time t is given by the following:

$$J = (A_x \exp(i\phi_x), A_y \exp(i\phi_y)) = \exp(i\phi_x)(A_x, A_y \exp(-i\delta)).$$

In practice, the factor $\exp(i\phi_x)$ is ignored, so that the state of polarization is described by the three main parameters: $A_x$, $A_y$ and $\delta$. The physical interpretation of these three parameters is most commonly based on the polarization ellipse, which describes the path traced out by the tip of the electric field vector in time at a particular location, or in space at a particular time. It should be noted that the Jones vector description is valid only for monochromatic light, or a single frequency component of a signal.

A more complete description of the state of polarization is based on the defined Stokes parameters, since this method also accounts for the degree of polarization (DOP) of a non-monochromatic signal. In terms of the Jones vector parameters, the four Stokes parameters are defined by:

$$S_0 = A_x^2 + A_y^2$$

$$S_1 = A_x^2 - A_y^2$$

$$S_2 = 2 A_x A_y \cos\delta$$

$$S_3 = 2 A_x A_y \sin\delta,$$

and the degree of polarization (DOP), $0 \leq DOP \leq 1$, is defined to be:

$$DOP = \frac{\sqrt{S_1^2 + S_2^2 + S_3^2}}{S_0}.$$

A partially polarized signal can be considered to be made up of an unpolarized component and a polarized component. The DOP is used to define that fraction of the signal which is polarized, and this fraction may be described by either the polarization ellipse or Jones vector. It is to be noted that, in strict terms, there are four parameters that are required to fully describe the elliptical signal: (1) the shape of the ellipse; (2) the size of the ellipse; (3) the orientation of the major axis; and (4) the sense of rotation of the ellipse. Thus, four measurements are required to unambiguously define the signal. These four parameters are often taken to be $A_x$, $A_y$, the magnitude of $\delta$, and the sign of $\delta$. The four Stokes parameters also provide a complete description of fully as well as partially polarized light. The Jones vector may be derived from the Stokes parameters according to:

$$A_x = \sqrt{S_0 + S_1}/\sqrt{2}$$

$$A_y = \sqrt{S_0 - S_1}/\sqrt{2}$$

$$\delta = \arctan(S_3/S_2)$$

It is to be noted that the last equation above does not unambiguously determine $\delta$. Most numerical implementations of $\theta = \arctan(x)$ define the resulting angle such that $-\pi/2 < \theta < \pi/2$. Thus, for $S_2 \geq 0$, the expression $\delta = \arctan(S_3/S_2)$, where for $S_2 < 0$, the expression $\delta = \arctan(S_3/S_2) \pm \pi$ should be used. Therefore, with the knowledge of the four Stokes parameters, it is possible to fully determine the properties of the polarized signal.

It has been recognized in accordance with the teachings of the present invention that the full state of polarization (SOP) cannot be determined by merely evaluating the signal passing through a single polarizer. Birefringence alone has also been found to be insufficient. In particular, a polarimeter may be based on a presumption that the optical signal to be analyzed is passed through a compensator (birefringent) plate of relative phase difference $\Gamma$ with its "fast" axis oriented at an angle C relative to the x axis (with the light propagating along the z direction). Further, it is presumed that the light is subsequently passed through an analyzer with its transmitting axis oriented at an angle A relative to the x axis. Then, it can be shown that the intensity I of the light reaching a detector disposed behind the compensator and analyzer can be represented by:

$$I(A, C, \Gamma) = \tfrac{1}{2}\{S_0 + S_1[\cos(2C)\cos(2[A-C]) - \sin(2C)\sin(2[A-C])\cos(\Gamma)] + S_2[\sin(2C)\cos(2[A-C]) + \cos(2C)\sin(2[A-C])\cos(\Gamma)] + S_3 \sin(2[A-C])\sin(\Gamma)\}.$$

In this case, $S_j$ are the Stokes parameters of the light incident on the compensator, such that $S_0$ is the incident intensity. If the compensator is a quarter-wave plate ($\Gamma = \pi/2$), then the intensity as defined above can be reduced to:

$$I(A, C, \pi/2) = \tfrac{1}{2}\{S_0 + [S_1 \cos(2C) + S_2 \sin(2C)]\cos(2[A-C]) + S_3 \sin(2[A-C])\},$$

Whereas if the compensator is removed altogether ($\Gamma = 0$), the equation for the intensity I reduces to:

$$I(A,-,0) = \tfrac{1}{2}\{S_0 + S_1 \cos(2A) + S_2 \sin(2A)\}.$$

This latter relation illustrates conclusively that it is impossible, without introducing birefringence, to determine the value of $S_3$, and hence the sense of rotation of the polarization ellipse.

Following from the equations as outlined above, a polarimeter may be formed using a compensator (for example, a quarter-wave plate), a polarizer, and a detector. In particular, the following four measurements, used in conventional polarimeters, unambiguously characterize the Stokes parameters:

1) no wave plate; no polarizer→$I(-,-,0) = S_0$
2) no wave plate; linear polarizer along x axis→$I(0,-,0) = \tfrac{1}{2}(S_0 + S_1)$
3) no wave plate; linear polarizer at 45°→$I(45,-,0) = \tfrac{1}{2}(S_0 + S_2)$
4) quarter-wave plate at 0°; linear polarizer at 45°→$I(45, 0, \pi/2) = \tfrac{1}{2}(S_0 + S_3)$.

In a conventional polarimeter using this set of equations, the measurements may be performed sequentially with a single compensator, polarizer and detector. Alternatively, the measurements may be formed simultaneously, using multiple components by splitting the incoming beam of light into four paths in a polarization-independent fashion.

In accordance with the teachings of the present invention, an in-line polarimeter comprises a plurality of gratings, formed sequentially in a section of optical fiber, in combination with an elliptical phase retarding element (hereinafter referred to as a "compensation element", such as a birefringent plate) to uniquely define the state of polarization of an optical signal. As is well known, fiber gratings are capable of coupling light out of the fiber, where the efficiency of this coupling can be tailored by controlling the induced index change and tilting the grating. Furthermore, the out-coupling efficiency for light exiting the fiber "nearly normal" to the fiber axis into a particular azimuthal direction is strongly dependent upon the polarization of the guided light incident on the grating. Therefore, the degree of selectivity with respect to polarization can be used to provide the required polarization-sensitive measurements. FIG. 1 illustrates an exemplary in-line, all-fiber polarimeter 10 formed in accordance with the present invention that utilizes this selectivity to provide a number of different polarization-sensitive measurements. As shown, an incident lightwave beam L is coupled into core region 12 of polarimeter 10. Incident beam L then impinges a first grating 14, where a predetermined intensity $I_1$ of incident beam will be out-coupled by first grating 14 and measured by a first detector 16. Presuming that light polarized in the plane of FIG. 1 to be p-polarized and normal to FIG. 1 to be s-polarized, first grating 14 is oriented such that only the s-polarized light will be coupled out and thereafter detected by first detector 16. In general, therefore, first grating 14 functions as an analyzer oriented along the x axis. In one embodiment of the present invention, an anti-reflective coating 15 may be disposed to cover fiber 12 in the vicinity of first detector 16 to prevent reflections from re-entering first detector 14. Alternatively, an index-matching epoxy can be used to bond the detector to the fiber. In general, any appropriate optical coupling arrangement can be used to suppress multiple reflections from impinging the detector.

The remaining portion of incident lightwave beam L then encounters a second grating 18, rotated 90° with respect to first grating 14. Therefore, second grating 18 will preferentially out-couple the p-polarized light (designated $I_2$), directing this signal toward a second detector 20 (that is, an analyzer disposed along the y axis of the signal). As an alternative to anti-reflective coating 15, an index-matching element 17 may be disposed between second grating 18 and second detector 20 to prevent reflected signals from re-entering the system. A third grating 22 is oriented at an angle of 45° with respect to both first grating 14 and second grating 18. Thus, the out-coupled light from third grating 22 (denoted $I_3$) will contain both an s- and p-polarized component and is detected by a third detector 24. The remaining incident lightwave beam L next passes through a quarter-wave plate 26 formed of a section of birefringent material. As is well-known in the art, the quarter-wave plate oriented at 0° functions to convert in 45° linearly polarized light into circularly polarized light and vice versa. Upon exiting quarter-plate 26, the beam L then impinges a fourth grating 28, oriented at 135°. The out-coupled portion of the signal is then detected by an associated detector 30, where the remaining lightwave signal becomes the optical output O from polarimeter 10.

Summarizing, polarimeter 10 of the present invention provides the measurement of the required Stokes parameters in the following fashion:

4) first grating 14: linear polarizer at 0°; $I(0,-,0)=\frac{1}{2}(S_0+S_1)$;

2) second grating 18; linear polarizer at 90°; $(90,-,0)=\frac{1}{2}(S_0-S_1)$;

3) third grating 22; linear polarizer at 45°; $I(45,-,0)=\frac{1}{2}(S_0+S_2)$; and 4) wave plate 26 and fourth grating 28; quarter-wave at 0° and linear polarizer at 135°; $I(135,0,\pi2)=\frac{1}{2}(S_0-S_3)$.

The desired Stokes parameters can then be recovered by inverting these equations, resulting in the following values:

$S_0=I(0,-,0)+I(90,-,0)$ $S_1=I(0,-,0)-I(90,-,0)$ $S_2=2I(45,-,0)-I(0,-,0)-I(90,-,0)$ $S_3=-2I(135,0,\pi/2)+I(0,-,0)+I(90,-,0)$.

Figure 2:
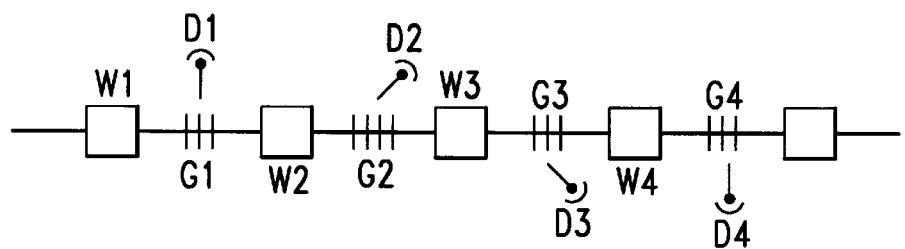
FIG. 2 is a generalized depiction of an in-line all-fiber polarimeter of the present invention.

As will be described in detail below, the arrangement of FIG. 1 is optimal in that the polarization is determined with the greatest accuracy for a given level of detector noise. However, in the general case (as shown in FIG. 2), the angles of gratings G1–G4 and the phase delay associated with a set of wave plates W1–W4 need not be as well-controlled and still provide valid useful data with respect to the state of polarization of an optical signal. The components must only be stable. In general, the four detector outputs (D1, D2, D3 and D4) are related to the state of polarization as follows: the input state of polarization is defined as $S^0$ and the state of polarization after each grating is defined as $S^i$. For the sake of discussion, the measurement recorded by the $i^{th}$ detector Di is defined as $P_i$. Since the $0^{th}$ component of the Stokes parameters, $S_0$, is proportional to the total intensity, $P_i$ must be proportional to the change in this quantity going through the $i^{th}$ grating Gi, defined as follows:

$P_i=k_i[S^i-S^{i-1}]_0$, where $k_i$ is determined by the coupling efficiency and calibration of the $i^{th}$ detector Di, and $P_i$ is corrected by subtracting the detector dark current signal value. $S^i$ and $S^{i-1}$ are related to each other by the Mueller matrix $M^i$ of detector Di as follows:

$S^i=M^i S^{i-1}$, and each $S^i$ is therefore related to the output Stokes parameter $S^4$ by:

$$S^4 = \left[\prod_{j=i+1}^{4} M^j\right] S^i.$$

From these two relations, it may be shown that there is a linear relationship between the four detector measurement quantities $P_i$ and the four Stokes components of output light $S^4_i$ by the following:

$$S^4_i = \sum_j N_{ij} P_j,$$

where N is defined as the "instrument matrix" which characterizes the polarimeter and relates any set of four detector measurements to the state of polarization at the output of the polarimeter of the present invention. Initially, the values for the instrument matrix may be determined by measuring the detector values when light of a known polarization is present at the output of the polarimeter. To fully calibrate the polarimeter, therefore, a set of four polarization states with linearly independent Stokes vectors S(m) must be produced at the output of the polarimeter. One possibility, for example, is linear polarization at 0°, 45°, 90° and right-hand circular polarization. These four states can be generated by placing a linear polarizer and quarter wave plate at the output, and nulling the throughput power for the appropriate orientations of the polarizer and wave plate using a polarization controller at the input of the polarimeter. For each polarization state $S^{(m)}$, a vector of the four detector values $P^{(m)}$ will be measured (hereinafter referred to as a "detector vector"). These vectors are related by the instrument matrix as follows:

$$S_i^{(m)} = \sum_j N_{ij} P_j^{(m)}.$$

Inversion of the four by four matrix $P_j^{(m)}$ (whose columns are the individual $P^{(m)}$) then gives $N_{ij}$;

$$N_{ij} = \sum_m S_i^{(m)} (P^{-1})_{mj}.$$

It is to be noted that this calibration procedure takes into account any set of grating alignments, as well as any orientation and degree of retardation associated with the wave plate. The calibration also takes into account polarization-dependent losses due to out-coupling from each grating. Moreover, the calibration can be referenced to either the output or the input. From the derivation of instrument matrix $N_{ij}$, it is evident that the only grating and wave plate combinations that cannot be used are those resulting in a singular instrument matrix, that is, a matrix $N_{ij}$ whose determinant is zero. In this case, there will be at least two input polarizations that yield the same detector values, and so the polarimeter cannot uniquely determine the output polarization. It can also be shown that instrument matrices that have relatively small determinants are more sensitive to detector noise and error. Briefly, this is due to the fact that there are now two polarization states that give very similar detector values, and if these two polarization states span a large region of the Poincare sphere, then small errors in the detector values will correspond to disproportionately large variations in the measured state of polarization. Alternatively, a near-singular matrix limits the fraction of the detector vector space that is mapped onto the measured Stokes vectors, thus making the system more prone to error due to detector error and noise. In the preferred embodiment, therefore, the detector powers are caused to vary through the entire space of detector vectors as the input polarization is changed, thus providing minimum sensitivity to errors and, as a result, maximum accuracy.

It is also to be noted that the arrangement of the detectors is critical to minimizing the polarization dependent loss (PDL) of the polarimeter. Two orthogonally oriented gratings with matched out-coupling efficiencies will have zero PDL, and in general, even if the gratings are not exactly orthogonal or matched in efficiency, an approximate orientation of this kind will reduce PDL to significantly less than that of a single grating. Therefore, another possible arrangement of the gratings is to place the waveplate between two pairs of orthogonally oriented gratings. No two elements may have the same orientation, however, since thus would result in a singular instrument matrix. As a result of this requirement, this configuration may be more susceptible to detector noise than the previously-discussed embodiment.

The following discussion is related to process details related to the arrangement of the present invention as depicted in FIG. 1. It is to be understood that the method of forming such an in-line, all-fiber polarimeter is considered to be general in nature and equally applicable to the generalized arrangement of FIG. 2. In general, during the fabrication of polarimeter 10 of the present invention, quarter-wave plate 26 is preferably formed using a UV exposure process. It is well known that the UV photosensitivity of optical fibers is inherently birefringent. In particular, a substantial fraction of the UV-induced birefringence is correlated to the polarization of the UV light—probe light polarized along the axis of the UV exposure light tends to experience a greater index of refraction than light polarized orthogonally with respect to the axis. In hydrogen-loaded fibers, the asymmetric index change across the core resulting from high absorption of the side UV radiation also contributes to the birefringence. The degree of UV-induced birefringence depends on many factors, and it has been observed to vary roughly between 0.1% to 10% of the total UV-induced index change. For a UV-exposed section of fiber to function as a quarter-wave plate, light polarized along the fast and slow axes must experience a relative phase difference of $(2\pi/\lambda)\Delta nL = \pi/2$, where $\Delta n$ is defined as the birefringence and L is the length of the UV-exposed section. That is, the length required for a quarter-wave plate is defined by the following:

$$L = \frac{\lambda(4m+1)}{4\Delta n},$$

where m is defined as a whole integer. For example, for a conservative estimate, it can be assumed that the UV-induced birefringence, $\Delta n$, is 1% of the total index change, $\delta n_{UV}$. If $\delta n_{UV} = 2 \times 10^{-3}$, then a length of $L \cong 2$ cm is required, which is a reasonable length to maintain a polarimeter of compact proportions.

In order to obtain the maximum polarization selectivity for light coupled out of a fiber by a grating, the light should exit the fiber nearly normal to the fiber axis. This requirement determines the grating period for a given wavelength. In particular, if the direction of the out-coupled light is given by the angle $\theta$ measured in air relative to the normal of the fiber axis, then the grating equation for first-order diffraction may be written simply as: $\sin \theta = n_{eff} - \lambda/\Lambda$, where $n_{eff}$ is the effective index of the guided mode, $\lambda$ is the predefined vacuum wavelength of the incoming optical signal, and $\Lambda$ is the period of the grating measured along the fiber axis. So, for example, to couple light out exactly normal to the fiber axis (i.e., $\theta = 0°$) with an input wavelength of 1550 nm, in a fiber with an effective index of about 1.45, requires a grating period of $\Lambda = 1070$ nm.

Almost all gratings are capable of coupling light of the appropriate wavelength out of the fiber at normal incidence, with the exception of an untilted grating that comprises a uniform perturbation over the entire transverse extent of the guided mode (i.e., one that extends out into the fiber cladding). However, for untilted gratings, the out-coupling efficiency is relatively small. Also, for these gratings, the out-coupling is circularly symmetric—the radiation pattern (including all polarizations) consists of a cone, or a disk for the case of normal out-coupling. Since polarimeter 10 of this particular embodiment of the present invention requires sufficient light at each detector 16, 20, 24 and 30 to maintain a reasonable signal-to-noise ratio, while also coupling the minimum amount of light possible out of the guided mode to minimize transmission loss, it is desirable to channel the light directionally toward the associated detectors. In particular, directional control can be accomplished by tilting (referred to in the art at times as "blazing") the gratings, as shown in FIG. 1. In particular, a 45° tilt is to known to provide the maximum directional selectivity and normal out-coupling efficiency for a given grating strength, while also providing broad wavelength bandwidth.

Figure 3:
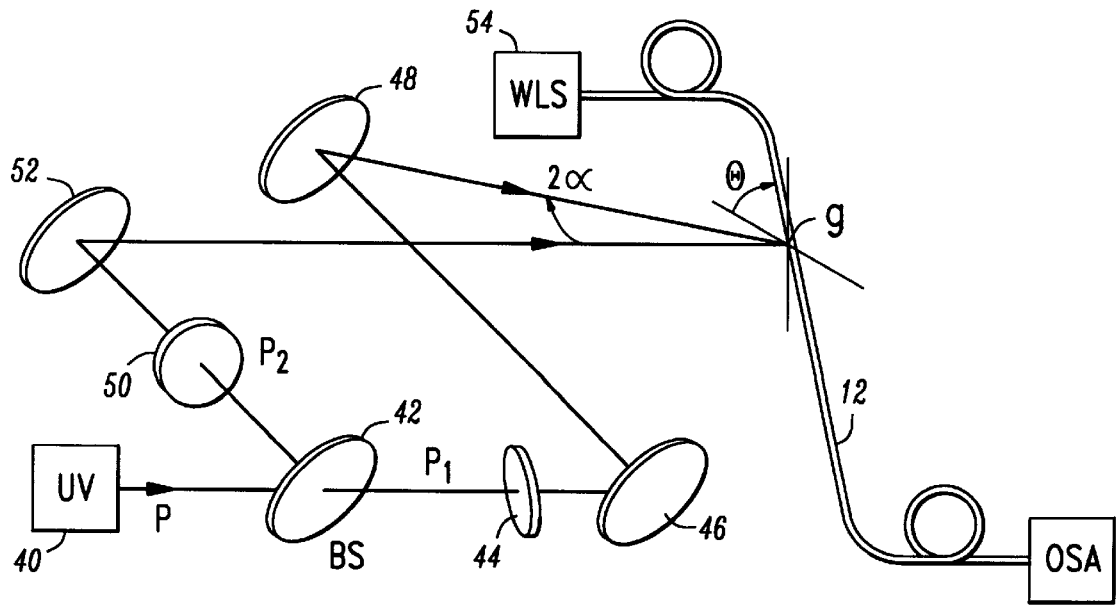
FIG. 3 contains an exemplary arrangement which may be used to form the blazed gratings in the polarimeter of the present invention.

FIG. 3 illustrates, in particular, an exemplary arrangement useful in forming 45° tilt gratings for an in-line all-fiber polarimeter of the present invention. In particular, the gratings are written using an interferometric technique with an excimer-pumped frequency-doubled, pulsed dye laser 40 ($\lambda_{UV}$=242 nm). The particular arrangement of FIG. 3 utilizes a white-light interferometer that ultimately produces two interfering beams separated by an angle 2α, as shown. Tilted grating fringes are achieved by rotating the fiber through an angle $\theta_{tilt}$ in the plane normal to the bisector of the two interfering beams. Light is focused onto the fiber using a 1-m focal length cylindrical lens in each arm of the interferometer. In particular and in referring to the arrangement of FIG. 3, the pulsed light output P from UV laser source 40 first impinges a beam splitter 42 which then splits the light into two, essentially equal components, denoted $P_1$ and $P_2$. First component $P_1$ is then focused by a first cylindrical lens 44 through a first mirror 46. The focused light is then reflected by first mirror 46 toward a second mirror 48, which then re-directs the focused beam onto location g of fiber 12. Second component $P_2$ of the pulsed signal from laser source 40 is similarly focused by a second cylindrical lens 50 through a third mirror 52, which then directs focused component $P_2$ toward fiber 12. As shown in FIG. 3, the various mirrors are oriented such that an angle of 2α is maintained between the two components as they interfere on the fiber surface.

Figure 4:
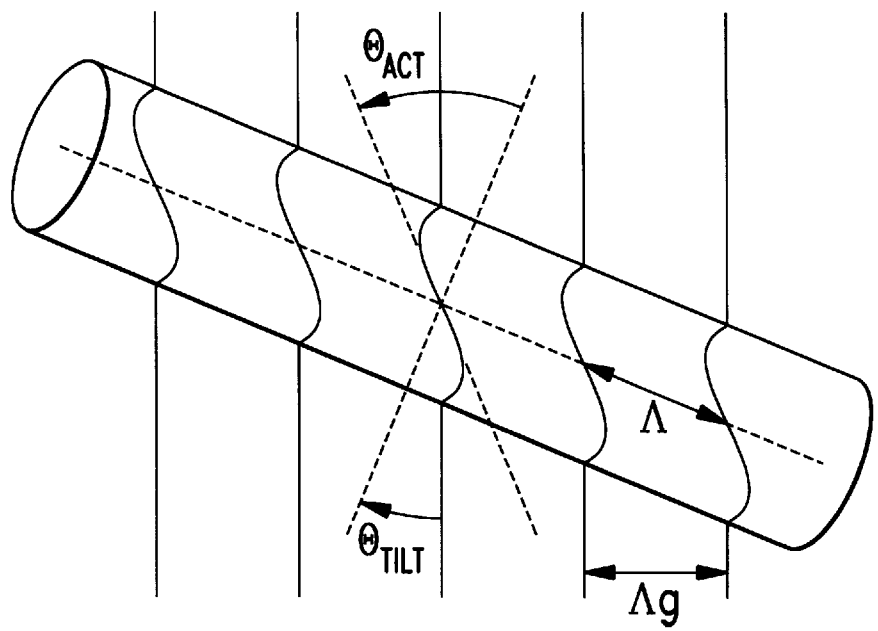
FIG. 4 illustrates the distortion of vertical interference fringes introduced by the cylindrical fiber contour.

It is to be noted that the cylindrical lensing effect of the fiber itself will distort the propagation of the UV light through the fiber, and needs to be considered when determining the proper tilt angle $\theta_{tilt}$. FIG. 4 illustrates precisely how this cylindrical lensing effect of the fiber distorts the fringes. Illustrated in FIG. 4 are the contours of peak intensity of the fringes in the plane of the fiber axis. Near the core, the distortion results in nearly linear fringes that are simply rotated with respect to the original fringe orientation in space. The UV light that reaches the core is almost normally incident on the surface of the fiber, and thus the behavior of this light may be approximated using paraxial rays refracting through a spherical surface. Using the rules of paraxial ray-tracing, therefore, it can be shown that the light would be focused a distanced f=Rn/(n−1) behind the surface of the fiber if the second fiber-air interface were absent, where R is the radius of the fiber and n=1.5 is the index of refraction for the glass fiber at λ=242 nm. Thus, at a distance R behind the front fiber surface, or at the fiber core, refraction of the collimated incident light rays decreases the height of each ray from the optical axis to exactly 1/n times the incident height. The effect of this demagnification on the fringes is to compress the fringes by a factor of 1/n along the direction normal to the fiber axis, in the plane of the fiber axis. As a result, the relationship between the fiber tilt angle $\theta_{tilt}$ and the fringe tilt angle $\theta_{act}$ can be defined by:

$$\tan \theta_{act} = n \tan \theta_{tilt}.$$

For the purposes of the present invention, the desired tilt angle $\theta^{act}$ is 45°. Therefore, the fiber itself should be tilted by an angle $\theta_{tilt}$ of 33.7°.

Once the fiber tilt angle $\theta_{tilt}$ and the desired grating period Λ along the fiber axis are known, the interferometer arrangement as illustrated in FIG. 3 can be appropriately configured. In particular, the period $\Lambda_g$ of the UV fringes in space, as shown in FIG. 4, is related to the desired period in the fiber by the following relation:

$$\Lambda_g = \Lambda \cos \theta_{tilt},$$

Given the above-defined values for both Λ and $\theta_{tilt}$, a value for $\Lambda_g$ is equal to 890 nm. This period is related to the half-angle ot between the two intersecting UV beams by the following:

$$\Lambda_g = \frac{\lambda_{UV}}{2 \sin \alpha}.$$

Therefore, for the arrangement as shown in FIG. 3, α=7.81°. Using these parameters, the interferometer is set up to make efficient, 45°-tilted out-coupling gratings for 1550 nm light.

Figure 5:
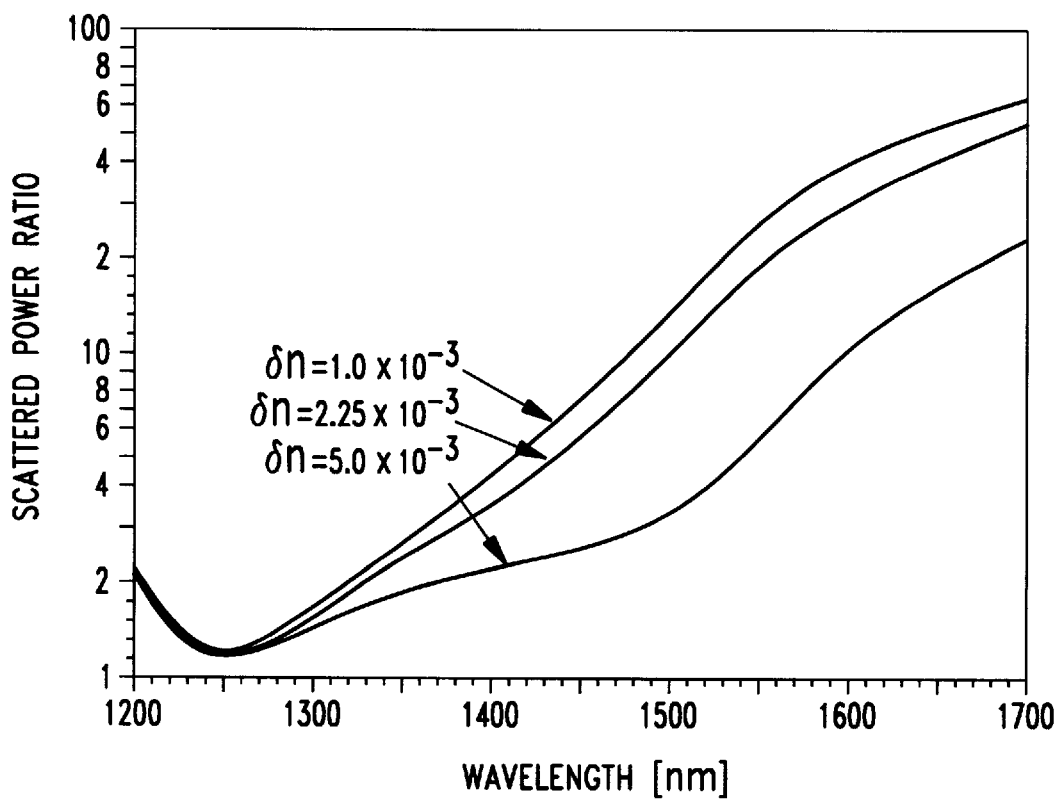
FIG. 5 is a graph illustrating the ratio of scattered power for s-polarization to p-polarization for three different grating strengths.

The performance of the gratings of the present invention as a "polarizer" within the in-line polarimeter can be understood by comparing the s- and p-polarized out-couplings directly. Since the actual signal measured on each detector is actually the scattered signal, the "extinction ratio" that determines the purity of the polarizer can be defined by the ratio of the scattered powers, or $S_s/S_p$. A theoretical prediction of this ratio is plotted (on a logarithmic scale) in FIG. 5 for three different grating strengths: δn=5.0×10$^{-3}$, δn=2.25×10$^{-3}$, and δn=1.0×10$^{-3}$. As shown, the extinction ratio improves at increasingly longer wavelengths, even as the out-coupling efficiency diminishes (as a result of the p-polarized efficiency decreasing at longer wavelengths). Further, it is shown that the extinction ratio is actually better for weaker gratings. The maximum total extinction ratio for the cases illustrated in FIG. 5 is slightly greater than 60. However, it is to be understood that this calculation is for the sum of the power scattered in all directions, and therefore does not apply to the extinction ratio for scattering into any one specific direction. In particular, while an appreciable amount of the p-polarized light is scattered by this grating, most of the light is coupled out along the axis of rotation of the tilted grating planes (that is, along the x direction for first grating 14 as shown in FIG. 1). In contrast, as discussed below, the s-polarized light is predominantly coupled out normal to the axis of rotation of the tilted grating planes (that is, along the −y direction for first grating 14 in FIG. 1). Consequently, the extinction ratio measured along the direction of maximum s-polarized out-coupling should be much greater than 60.

Figure 6:
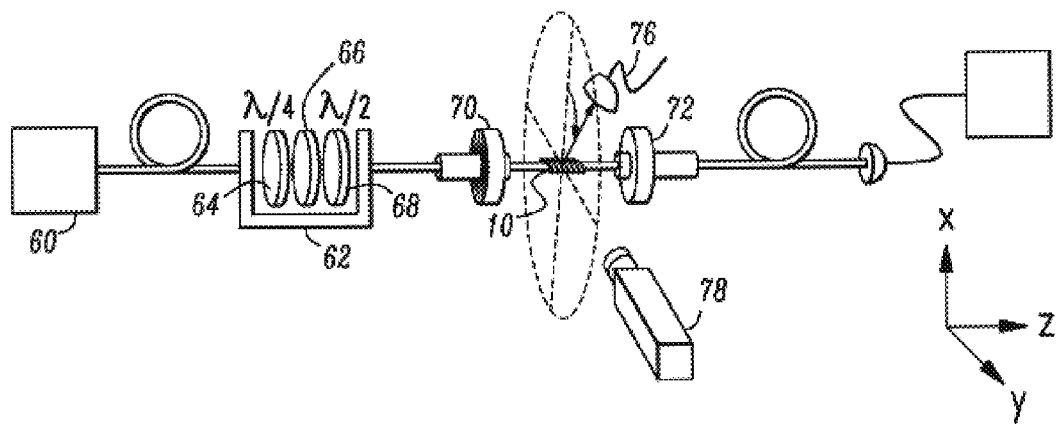
FIG. 6 illustrates an exemplary apparatus useful in analyzing the out-coupled light from a tilted grating formed in accordance with the present invention.

An arrangement for directly measuring the out-coupling from an exemplary grating within a polarimeter of the present invention is illustrated in FIG. 6. A single-frequency, tunable laser source 60 provides the input signal used for measurement purposes. A following polarization controlling arrangement 62 including a quarter-wave plate 64, polarizer 66 and half-wave plate 68 is used to obtain predetermined states of polarization to be incident on the grating being tested. In particular, quarter-wave plate 64 and polarizer 66 are adjusted to produce maximum available power in a linearly polarized state. Half-wave plate 68 is then rotated to orient the linear polarized light along a desired direction. The grating is mounted (in an untwisted stated) in a pair of rotatable fiber chucks 70,72 so that it can be precisely aligned for maximum out-coupling along the y axis (as shown in FIG. 6). Alignment can be accomplished by launching a 633 nm HeNe laser into the grating and observing the out-coupled radiation directly. Fiber section 74 between polarization controller 62 and the grating is about 20 cm long and straight, so as to ensure that the state of polarization produced in controller 62 is maintained at the grating. An infrared detector 76 measures the scattered power as a function of either the angle φ about the fiber axis or the transmitted power. An infrared video camera 78 can also be used to measure the pattern of scattered radiation.

Figure 7:
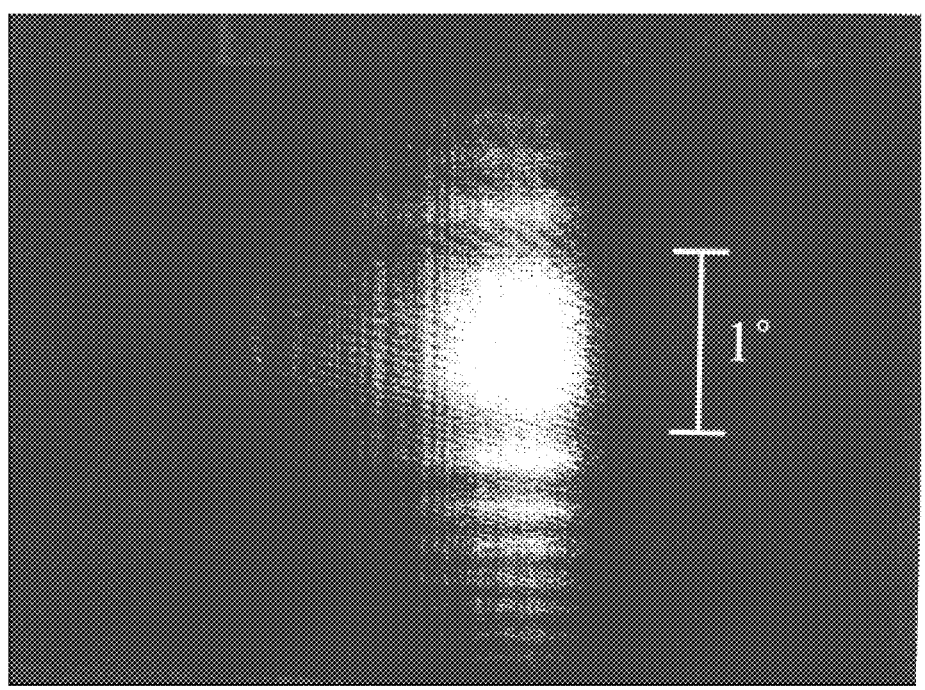
FIG. 7 is a video representation of the far-field radiation pattern from a tilted grating using s-polarized light.

FIG. 7 illustrates a captured image of a far-field radiation pattern scattered by a grating, with camera 78 oriented as shown in FIG. 6, with the sensor approximately 60 mm from the grating. Light incident on the grating was linearly polarized parallel to the x axis, thus producing s-polarized scattering along the y direction. As seen in FIG. 7, the scattered intensity is highly directional, as desired for providing maximum coupling into the associated detector.

The above-described embodiment of the present invention is presumed to be limited in the sense that it can only perform an accurate polarization characterization for a single incident wavelength, since there is no means at a single detector to distinguish the relative intensity contributions from multiple, simultaneous wavelengths. It is recognized that in some instances it would be valuable to provide polarization characterization information for multiple wavelengths simultaneously propagating through the transmission fiber. Thus, an alternative embodiment of the present invention is realized by substituting a detector array, oriented along the fiber axis, for each single detector element. In this arrangement, the detector array can be used to exploit the fact that different wavelengths will diffract out of the fiber at slightly different angles. This multi-wavelength approach is well-known for simple tap arrangements including gratings, where improved wavelength resolution is obtained by focusing the out-coupled beam at the detector array using a small amount of chirp in the grating, an independent bulk lens element, or a bending of the fiber grating with an appropriate radius of curvature.

The detector array polarimeter embodiment useful for multiple wavelength applications is considered, however, to have some limitations. First, the detector arrays are comparably quite expensive with respect to single detector elements—a cost increase would be incurred for each of the four required detector elements. In addition, the detectors will always have finite wavelength resolution, below which two independent signals could not be resolved. A critically important instance of this situation is the case of two signals with orthogonal polarizations that are very nearly the same wavelength (or perhaps even the exact same wavelength). Such orthogonal signals will be used in future communication systems and cannot be resolved with a detector array. Another multi-wavelength and multi-signal approach is to detect the relative amplitude of radio frequency (RF) tones that are specifically encoded for identification purposes on each channel. This relative RF amplitude information is derived from the detector intensity output but can simultaneously detect the RF amplitudes at multiple frequencies. This approach is well known and has been proposed for monitoring the intensity of wavelength division multiplexed (WDM) communication systems. When implemented in the system of the present invention, the added cost of detector arrays is avoided, while still enabling the simultaneous polarization monitoring of two independent orthogonal signals at the same wavelength. These advances come with the difficulty of having to add RF tones to the detected signals and keep track of these tones, so the preferred arrangement for implementing a multi-wavelength polarimeter will ultimately depend upon the application.

It is to be understood that, in its most general form, an all-fiber in-line polarimeter of the present invention may utilize less than four grating/detector combinations. Using three gratings, for example, will provide some data (albeit incomplete) regarding the state of polarization of an optical signal passing through the polarimeter. There may be circumstances, however (such as in an arrangement using polarization maintaining fiber for transmission) where some polarization-related information is known a priori and fewer than four gratings are sufficient to supply the missing information.

What is claimed is:

1. An in-line optical fiber polarimeter comprising a set of at least four gratings, disposed in any order, along the optical fiber, each fiber grating for out-coupling a separate one of a set of four polarization states from an incoming optical signal into an associated set of at least four detectors oriented at azimuthal angles $\theta_1$, $\theta_2$, $\theta_3$ and $\theta_4$ with respect to the propagation direction; and at least one elliptical phase retarder element disposed at a predetermined location along the optical fiber with respect to the set of gratings, said phase retarder defined by two principle polarization states $S_1$ and $S_2$, and a retardation angle $\Gamma$, said elliptical phase retarder disposed between any two of the gratings such that $S_1$ and $S_2$ are different from the polarizations out-coupled by at least one adjacent grating on each side, wherein the combination of the at least one elliptical phase retarder element with the set of at least four gratings provides an arrangement such that the linear polarization state out-coupled by each grating represents a unique state of polarization at the input of the polarimeter and the detector values allow for determination of the state of polarization.

2. An in-line optical fiber polarimeter as defined in claim 1 wherein the polarimeter comprises an all-fiber device with each grating comprising a fiber grating and the at least one elliptical retarder comprising a section of birefringent fiber.

3. An in-line optical fiber polarimeter as defined in claim 1 wherein at least one grating comprises a blazed grating.

4. An in-line optical fiber polarimeter as defined in claim 3 wherein each grating comprises a blazed grating.

5. An in-line optical fiber polarimeter as defined in claim 3 wherein an anti-reflection coating is included on the surface of the optical fiber to prevent multiple reflections into the detectors.

6. An in-line optical fiber polarimeter as defined in claim 3 wherein the polarimeter further comprises an optical coupling structure that transfers out-coupled light from the grating to the associated detector while minimizing multiple reflections into the detector.

7. An in-line optical fiber polarimeter as defined in claim 6 wherein the out-coupling efficiency is essentially flat to 3 dB over a bandwidth in excess of 10 nm.

8. An in-line optical fiber polarimeter as defined in claim 3 wherein the set of at least four gratings comprise a set of four gratings oriented, at azimuthal angles of 0°, 90°, 45° and 135°, and the elliptical retarder comprises a quarter wave plate oriented at 0°, wherein the principle states $S_1$ and $S_2$ are linearly polarized at 0° and 90°, the retardation angle is 90°, and the elliptical retarder is disposed between the 45° and 135° gratings.

9. An in-line optical fiber polarimeter as defined in claim 3 wherein the set of at least four gratings comprise a set of four gratings oriented, at azimuthal angles of 0°, 90°, 60° and 150°, and the elliptical retarder comprises a quarter wave plate oriented at 0°, wherein the principle states $S_1$ and $S_2$ are linearly polarized at 30° and 120°, the retardation angle is 90°, and the elliptical retarder is disposed between the 90° and 60° gratings.

10. An in-line fiber polarimeter as defined in claim 3 wherein the set of at least four gratings and at least one elliptical retarder are arranged so as to provide for minimal polarization-dependent loss on an optical signal passing therethrough.

11. An in-line fiber polarimeter as defined in claim 3 wherein the set of at least four gratings and at least one elliptical retarder are arranged so as to provide for maximum accuracy with respect to detector noise.

12. An in-line fiber polarimeter as defined in claim 3 wherein at least one fiber grating comprises an interferometric-produced grating.

13. An in-line fiber polarimeter as defined in claim 12 wherein UV-induced birefringence is used to produce the grating.

14. An in-line fiber polarimeter as defined in claim 3 wherein the elliptical retarder comprises a section a birefringent fiber.

15. An in-line fiber polarimeter as defined in claim 13 wherein the general retarder comprises UV-induced birefringence.

16. An in-line optical fiber polarimeter as defined in claim 14 wherein the section of birefringent fiber comprises a length L defined by $\lambda(4m+1)/4\Delta n$, where $\lambda$ is the optical signal wavelength, m is a whole integer and $\lambda n$ is the UV-induced birefringence.

17. An in-line optical fiber polarimeter as defined in claim 1 wherein the incoming optical signal comprises multiple wavelengths and the set of at least four detectors comprises a set of at least four detector arrays, the separate detectors within each array receive a separate wavelength of the multiple wavelengths contained within the incoming optical signal.

18. An in-line optical fiber polarimeter as defined in claim 17 wherein each grating comprises a chirped grating so as to focus the out-coupled light into the associated detector array.

19. An in-line optical fiber polarimeter as defined in claim 17 wherein the polarimeter comprises a set of at least four bulk lens elements, each element disposed between a fiber grating and its associated detector array, the bulk lens elements for focusing and improving resolution of the signals impinging the associated detector array.

20. An in-line optical fiber polarimeter as defined in claim 17 wherein at least fiber grating exhibits a bend sufficient to improve coupling between the grating and the associated detector array.

21. An in-line optical fiber polarimeter as defined in claim 1 wherein the incoming optical signal comprises multiple information signals, at least one of which has an RF tone encoded to allow for the associated detectors to distinguish the relative intensity of at least one of the received signals.

22. An in-line optical fiber polarimeter as defined in claim 21 wherein at least two of the information signals propagate at different wavelengths.

23. An in-line optical fiber polarimeter as defined in claim 21 wherein at least two of the information signals exhibit different polarization states.

24. An in-line optical fiber polarimeter as defined in claim 3 wherein the entire fiber comprising the polarimeter is a birefringent fiber.

* * * * *